United States Patent [19]

Sterzer

[11] 4,197,860
[45] Apr. 15, 1980

[54] HYPERTHERMIA APPLICATOR

[75] Inventor: Fred Sterzer, Princeton, N.J.

[73] Assignee: RCA Corporation, New York, N.Y.

[21] Appl. No.: 853,585

[22] Filed: Nov. 21, 1977

[51] Int. Cl.² ............................................... A61N 5/02
[52] U.S. Cl. ..................................................... 128/804
[58] Field of Search .............. 128/2 H, 404, 399, 783, 128/804; 219/10.55 R, 10.55 B, 10.55 E, 10.55 F, 10.55 M; 73/355 R, 355 EM

[56] References Cited

U.S. PATENT DOCUMENTS

| 2,407,690 | 9/1946  | Southworth ......................... 128/422      |
| 2,813,185 | 11/1957 | Smith ............................ 219/10.55 R    |
| 3,221,132 | 11/1965 | Staats ............................ 219/10.55 F   |
| 3,527,227 | 9/1970  | Fritz ........................... 219/10.55 R X  |
| 3,587,110 | 6/1971  | Woodward ......................... 343/813        |
| 3,939,319 | 2/1976  | Tamano et al. ................ 219/10.55 B        |
| 4,049,938 | 9/1977  | Ueno ............................. 219/10.55 R   |

FOREIGN PATENT DOCUMENTS

| 1489885  | 5/1969  | Fed. Rep. of Germany ........... 128/404    |
| 2304500  | 8/1974  | Fed. Rep. of Germany ........... 128/404    |
| 2462165  | 4/1976  | Fed. Rep. of Germany .... 219/10.55 B       |
| 342419   | 2/1931  | United Kingdom ..................... 128/804 |
| 431672   | 7/1935  | United Kingdom ..................... 128/804 |
| 446660   | 5/1936  | United Kingdom ..................... 128/804 |
| 479735   | 2/1938  | United Kingdom ..................... 128/804 |
| 502167   | 3/1939  | United Kingdom ..................... 128/804 |
| 762734   | 12/1956 | United Kingdom ..................... 128/804 |
| 862646   | 3/1961  | United Kingdom ..................... 128/804 |
| 1010922  | 11/1965 | United Kingdom ................. 219/10.55   |

OTHER PUBLICATIONS

Johnson, H. C., "Speed Sensors for Locomotives," RCA Engineer, vol. 22 No. 22, Aug.-Sep. 1976.
Guy, A. W. et al., "Determination of Power Absorption in Man Exposed to HFEM Fields by Thermographic Measurements on Scale Models," IEEE Biomed Engr Trans vol. BM-23, No. 5 pp. 361-371 Sep. 1976.
Wollins, B. "Cancer Therapy, Detection Aided by Microwave Technology," Microwaves Sep. 1977 pp. 22-24.
Barrett, A. H. et al., "Subcutaneous Temperatures: A Method of Non-Invasive Sensing," Science vol. 190 Nov. 14, 1975 pp. 669-671.
Davis, G., "Microwave Score TKO in Fight Against Cancer," Microwaves Oct. 1976 pp. 14,16.

Primary Examiner—Robert W. Michell
Assistant Examiner—Francis J. Jaworski
Attorney, Agent, or Firm—Samuel Cohen; Robert L. Troike

[57] ABSTRACT

There is disclosed an apparatus for hyperthermia treatment which distributes irradiating microwave signals into and throughout the treated tissue generating heat within the tissue at a substantially equal temperature distribution. The apparatus utilizes a hyperthermia applicator encased in a flexible material to conform to the surface of the tissue to be heated. The applicator provides microwave signals for irradiation into the treated tissue whereby substantially equal temperatures are generated throughout the treated tissue. The applicator further includes mode stirring to improve the distribution of heat more uniformly within the treated tissues.

3 Claims, 2 Drawing Figures

HYPERTHERMIA APPLICATOR

CROSS REFERENCE TO RELATED PATENT APPLICATIONS

Of interest are the following United States patent applications, Ser. No. 808,292, filed on June 20, 1977, entitled "Apparatus for Hyperthermia Treatment," by Fred Sterzer, and Ser. No. 853,587, filed Nov. 21, 1977, entitled "Current Tapered Corporate Antenna," by Jerome Rosen.

BACKGROUND OF THE INVENTION

1. Field of the Invention

This invention relates to an apparatus for hyperthermia treatment.

2. Description of the prior Art

Medical practitioners have known that a patient with a cancerous tumor can be successfully treated, by a process which raises the temperature of the tumor. This treatment is generally referred to as hyperthermia. One method of hyperthermia treatment is the use of microwave radiation energy. The temperature of the tissue irradiated by microwave energy is a function of the power or intensity of the microwave signal applied to the surface of the body tissue. The depth of penetration of a microwave signal into the tissue is an inverse function of the signal frequency employed. The volume of the tissue to be treated is controlled by the electrical and geometrical design of the microwave applicator. It is known that a flexible applicator can be utilized to conform to irregular surfaces. Such an applicator is described in U.S. Pat. No. 2,407,690, issued Sept. 17, 1946, to G. E. Southworth as illustrated by FIG. 7 thereof.

It is also known that remission of a tumor can be effected by elevating its temperature to 43.0°±0.5° C. It is desirable to provide for an equal temperature distribution within the treated tissue.

Prior methods of hyperthermia treatment employ a microwave-waveguide applicator to supply a microwave signal for the irradiation of the treated tissue. The distribution of the irradiating signal from the microwave-waveguide applicator is manifested as a pattern of standing waves of the operating frequency. The standing wave distribution produces maximum and minimum voltage points which develop non-uniform irradiating signals, correspondingly, producing undesirable non-uniform heating of the treated tissue.

SUMMARY OF THE INVENTION

The present invention provides for hyperthermia treatment with uniform heating of the tissue by microwave energy. A surface conforming hyperthermia applicnator distributes microwave energy into the tissue to heat the treated tissues.

DESCRIPTION OF THE PREFERRED EMBODIMENT

Figure 1:
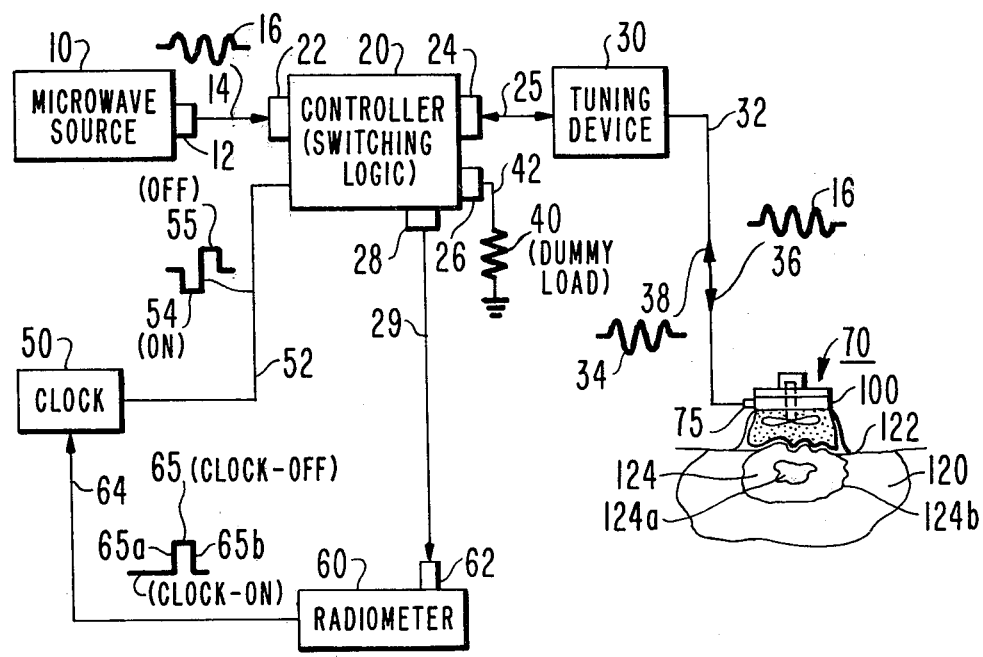
FIG. 1 is a block schematic of the preferred embodiment of the invention.

FIG. 1 illustrates the arrangement and organization of the main components of the preferred embodiment of the invention.

The hyperthermia apparatus includes a microwave source 10, providing a microwave signal 16, coupled over path 14 by connectors 12 and 22 to a controller 20. Controller 20 selectively couples the microwave signal 16, via connector 24 and tuning device 30 (in the direction of arrowhead 36) to applicator 70. Applicator 70 converts the microwave signal 16 into a distributed electromagnetic field for irradiating tissue 120 at predetermined time intervals under control of clock 50. The electromagnetic field is thus a pattern of spatially distributed electromagnetic energy. The distributed irradiating electromagnetic energy field is periodically interrupted by clock 50 to allow the tissue 120 to radiate a signal 34 (in the direction of arrow 38) for measurement by a radiometer 60 coupled to controller 20 via conductor 29 and connectors 28 and 62. Signal 16 is a relatively high-power energy signal which is converted to a distributed electric field for irradiating tissue 120, and signal 34 is a relatively low-power signal of radiated energy emanating from the heated tissue 120. Source 10 is a known tunable microwave signal generator capable of providing radio frequency signals in the frequency spectrum in the order of 100 to 10,000 MHz, and at signal power levels of 1.0 to several hundred watts. Source 10 is adjusted to provide a signal at terminal 12 at a predetermined frequency to effect the desired depth of penetration into the body tissue and at a predetermined power level for the desired heating of the tissue as indicated above.

Controller 20, comprising suitable switching logic, in response to clock 50 as will explained hereinafter, routes microwave signal 16 to either applicator 70, via input microwave path 14 output connector 24 and tuning device 30, or to dummy load 40 via input microwave path 14 and an output connector 42. Dummy load 40 has an impedance equal to the characteristic impedance of the source 10 and thus provides the proper termination for source 10 when source 10 is not coupled to the tissue 120. The tuning device 30 provides for impedance matching of the source 10 and thus the applicator 70 to the tumor 124 in a manner well known in the art. A suitable controller 20 is described in the above-identified patent application, Ser. No. 808,292.

Figure 2:
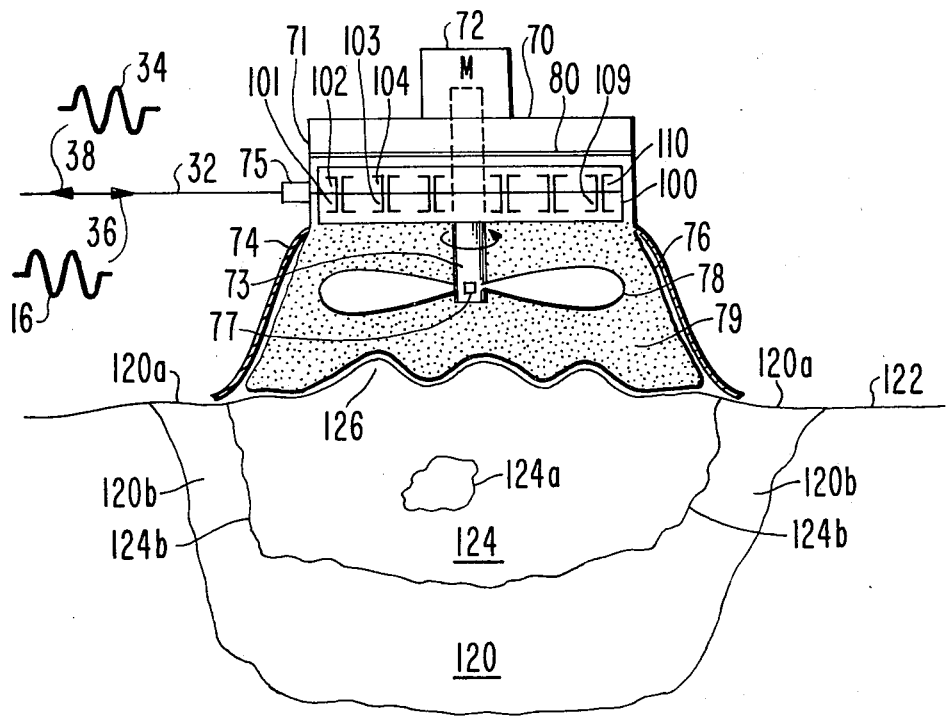
FIG. 2 illustrates in detail the applicator 70 shown in FIG. 1.

Applicator 70 is formed with a flexible bag 76 which conforms to the contour of surface of tissue 120 as shown better in FIG. 2. Furthermore applicator 70 functions to convert the microwave signal 16 into a distributed electrical field for irradiation of tissue 120. Applicator 70 is filled with a free-flowing dielectric powder 79 having a dielectric constant in the range of 5 to 50. The powder 79 may be of the name-brand ECCO-FLO HiK manufactured by Emerson and Cuming, Inc., Canton, Massachusetts, having a dielectric constant of 12. The connector 75 of the applicator 70 is connected to controller 20 via suitably, a 50 ohm coaxial line 32, tuning device 30, suitably a 50 ohm coaxial line 25, and a connector 24 of any suitable type. Applicator 70 ideally should match the impedance of the tissue 120. In practice, ideal matching is quite difficult. Nevertheless, the nearer the impedance match the better the performance of the applicator.

Radiometer 60 is of a known type that measures radiant energy and is preferably tunable to a selected band of frequencies in the microwave range, more particularly, in the frequency range of a microwave signal 16. Radiometer 60 is suitably calibrated or otherwise arranged to provide a signal representing the average temperature of the heat energy measured. Furthermore, radiometer 60 is provided preferably with a sensor circuit (not shown) that operates to generate over its output path 64, a temperature control signal 65 which is used to maintain a predetermined temperature range within tissue 120 (e.g., 43.0°±0.5° C.) corresponding to the measured radiant energy applied to its input connector 62, as will be explained further. When the temperature of the radiant energy sensed by the radiometer 60 is approximately 43.5° C. (the higher value of temperature in the predetermined operating range), the leading edge 65a of signal 65 is generated. Signal 65 serves to inhibit further heating of the tissue 120 as will be explained. Signal 65 is continued until the temperature drops to approximately 42.5° C. whereupon the radiometer causes signal 65 to return to its lower level as indicated by the trailing edge 65b.

Clock 50 provides time control signals 54 and 55 to controller 20. Control signal 54 defines the "ON" period during which the microwave signal 16 from source 10 is applied to tissue 120 and the microwave signal 16 is absorbed by and thus heats tissue 120. Control signal 55 defines the "OFF" period during which the microwave signal 16 from source 10 is switched to dummy load 40 and the radiometer 60 is connected to applicator 70 to measure the radiant energy from the tissue 120. A suitable clock 50 is described in the aforementioned application, Ser. No. 808,292. Clock 50 in response to signal 65 from radiometer 10, causes controller 20 to couple th energizing signal 16 from applicator 70 to dummy load 40 and to connect radiometer 60 to measure the radiated energy signal 34 from the tissue 120. In this condition of not being exposed to the energizing signal 16, the tissue temperature will tend to reduce by the loss of heat to the cooler surrounding tissue and to the applicator. When the temperature of tissue 120 reaches approximately 42.5° C. as sensed by the radiometer 60, signal 65 is caused to return to its lower level to thereby switch signal 16 back to energizing the tissue 120 via applicator 70 and simultaneously to disconnect radiometer 60 from line 25, thereby preventing it from damage by the higher energy values of signal 16.

Reference is now made to FIG. 2 illustrating in detail the hyperthermia applicator 70.

Applicator 70 receives signal 16 via a distributed network of antennas formed as a corporate antenna 100 positioned within an aluminum housing 71. A suitable corporate antenna is described in U.S. Pat. No. 3,587,110, issued June 22, 1971 to O. M. Woodward entitled "Corporate-Network Printed Antenna." Corporate antenna 100 includes planar dipole antennas 101, 102, 103, 104, . . . 109 and 110, disposed alternately on opposite sides of a substrate. The planar dipole antennas are arranged to radiate microwave signals in a pattern that is substantially downwardly into the dielectric material 79 of applicator 70. Radiated microwave signals that are beamed upwardly are reflected by reflector 80 which is suitably positioned to reflect signals from its surface to be propagated downwardly to thereby reinforce the other signals propagating into the dielectric material 79.

Dielectric material 79, as previously described, is a free-running dielectric powder having a dielectric constant such as 12, although powders of higher dielectric constants are preferable. Dielectric material 79 is distributed within a flexible bag 76 which is of a polyethylene material that is pervious to the microwave signals. Flexible bag 76 filled with the free-running dielectric material 79 provides the desired flexibility of applicator 70. This flexibility allows the applicator 70 to conform to surfaces to which it is applied, such as surface 122. Thus, the applicator 70 conforms to irregular surfaces such as an irregular surface contour illustrated as 126 of the FIG. 2.

Shielded skirt 74 is formed of a flexible mesh material which fits over the flexible bag 76 and extends sufficiently beyond the bag to conform to surface 122. The flexible mesh material is suitably a fine stainless steel 2 millimeter wire formed into 5 by 5 millimeter mesh. Skirt 74 located at the periphery of applicator 70, prevents microwave radiation outwardly from applicator 70 and the tissue over which it is applied.

A metal fan blade 78 is connected by a suitable screw connection 77 to shaft 73 of a motor 72. Shaft 73 is rotated suitably at a speed of 2 revolutions per minute. The rotating metal blade 78 performs the function of mode stirring, i.e., the blade 78 helps smooth the heating patterns in the tissue 120. Mode-stirring is well known in the microwave oven art. Mode-stirring for ovens is described in U.S. Pat. No. 2,813,185, entitled "Heating Devices," issued to Robert V. Smith on Nov. 12, 1957.

Refer now to FIG. 2. Microwave signal 16 is applied to applicator 70 via connector 75 which in turn is connected to corporate antenna 100. Corporate antenna 100 having a plurality of dipole antennas, radiates the microwave signal 16 into applicator 70 as radiant energy in the form of a plurality of electromagnetic field patterns. Tissue such as a cancerous tumor of the type that may be treated by the hyperthermia apparatus is illustrated as portion 124 of FIG. 2. The applicator 70 couples the radiated energy into tumor 124 and surrounding tissue 120 that lies in the electromagnetic field patterns. This radiant energy irradiates and thereby raises the temperature of tumor 124 and tissue 120. The projected radiant field pattern can be confined to the size of the tumor by adjustment of the shielded skirt 74. It is preferred that the heating effect be manifested only in the tumor 124 and not in surrounding tissue 120. In practice, it is a matter of choice of how to minimize the heating of tissue that should not be exposed to the radiant energy from the applicator 70.

Tumor 124 being heated by the irradiating energy generates radiant energy which is received and converted by the corporate antenna 100 into signal 34. Signal 34 is coupled back to controller 20 in the direction of arrowhead 38. Controller 20 couples signal 34 to radiometer 60 in the manner to be described further. Radiometer 60 is turned to the frequency of the microwave signal 16. Signal 34 represents the heat energy of tissue 124 and thus manifests the heat absorbed in the tissue 124. By measuring signal 34 in the manner detailed in the aforementioned application, Ser. No. 808,292, the average temperature of the volume of the tissue 124 irradiated by signal 16 is determined.

Thus, controller 20 couples the heating signal 16 to applicator 70 for irradiation of tumor 124 for a first predetermined time period and then couples the temperature indicating signal 34 to radiometer 60 for a second time period for the determination of the average temperature measurement of the heated tissue. A typical on-time for irradiation of tumor 124 is 5.0 seconds and a typical off-time for measurement of signal 34 is 1.5 seconds. These predetermined on-off time periods are determined by clock 50. The on-off periods are continued whereby the temperature of tumor 124 is raised and maintained within the critical temperature range of 43.0°±0.5° C. The on-off periods, i.e., the irradiation-measurement periods, are overridden or interrupted if the temperature of tumor 124 increases to a value approaching the upper limit (43.5° C.) of the critical temperature which would undesirably overheat the tumor. The radiometer 60 is suitably calibrated to sense this potential over-heating condition and to generate an override which is in the form of signal 65. Clock 50, in response to signal 65, provides signal 55 to controller 20 to switch signal 16 from the applicator 70 to load 40. Thereafter, when the temperature of tumor 124 drops to approximately 42.5° C., the lower temperature of the desired treatment temperature range, radiometer 60 recycles the system by signal 65, etc., to irradiate the tumor 124 and measure its temperature as described above.

The microwave signal 16 is coupled to the applicator 70 and then to corporate antenna 100 as described above. The corporate antenna 100 distributes signal 16 to the component planar dipole antennas 101, 102, 103, 104 ... 109 and 110. The dipole antennas radiate microwave signals that are confined to be downwardly into the dielectric material 79 of the applicator 70 by the radiation patterns of the antennas and the reflections by reflector 80 and skirt 74. Each planar dipole antenna radiates an electric field pattern into applicator 70. The plurality of the antennas 101, 102, 103, 104 ... 109 and 110, radiate energy in the form of a plurality of electric field patterns established within applicator 70. With a uniform array of antennas, the radiated energy is spread throughout the applicator in a relatively uniform distribution. The applicator 70 confines this uniformly distributed radiated energy toward tumor 124, and enters the tumor 124 over the skin in contact with applicator 70. The radiated energy penetrates the tumor 124 according to the distributed pattern of the fields heading the tumor 124.

This well-known phenomenon as described in detail in the aforementioned copending copending application, Ser. No. 808,292, is manifested in the temperature vs. depth profile effects of microwave irradiation.

According to another embodiment of the invention, tumor 124 is irradiated with a non-uniform distribution of the microwave signals. Proper distribution of energy applied to a tumor (124) can compensate for cooling that occurs in the lateral peripheral regions 124b of the treated tumor 124 within the untreated tissue 120. This cooling effect of untreated tissue 120 functioning essentially as a heat sink via the adjacent tissue portions 120a develops a temperature gradient within tumor 124 whereby the temperature at the central portion. (124a) is higher than at the peripheral surface 124b. This temperature gradient is compensated for or offset by irradiating the peripheral regions 124b of the tumor with a higher concentration of microwave signals than at the central portion 124a. A higher concentration of microwave signals at the peripheral regions 124b of tumor 124 is achieved by providing a larger concentration of dipole antennas (101, 102, etc.) in the peripheral regions of corporate antenna 100 than at the central portion. With this arrangement the intensity of the radiated signal from corporate antenna 100 into applicator 70 is greater in the peripheral regions of the applicator. Thus, the increase of microwave signal intensity correspondingly causes a greater heating effect to compensate for the peripheral heat loss and also to reduce relatively the heating effect in the central portion 124a.

Non-uniform distribution of the irradiated energy into tumor 124 may also be provided by appropriate power distribution of the microwave signal 16 to the dipole antennas on the corporate antenna 100. According to this feature of the invention, a higher concentration of power from signal 16 is distributed to the dipole antennas at the peripheral regions of corporate antenna than at the central region. Power distribution techniques for corporate antenna arrays are well known. A preferred non-uniform array is described in the above-identified application, Ser. No. 853,587. Such techniques are utilized to achieve the power distribution by dimensioning the power feed lines of the peripheral antennas and the central antennas so that the impedances of the array achieve the desired power distribution. The higher power transmitted from the peripheral antennas correspondingly causes the peripheral surfaces 124b of the treated tumor to be heated with a higher level of irradiation than the central portion 124a.

According to the preferred embodiment of the invention, uniform distribution for irradiating tumor 124 is achieved by mode-stirring. Mode-stirring is accomplished by rotating fan blade 78 at a slow speed, e.g., 1 rpm, within the electric fields emanating from corporate antenna 100. The rotating fan blade 78 cylically presents a short-circuit to the electric fields at the point of contact with fan blade 78. This short-circuit disturbs the electric field distribution, sometimes referred to as mode patterns, within applicator 70. This cyclic disturbance distorts or "smears" the standing waves within applicator 70 and also within the treated tumor 124. The standing waves that are being disturbed are otherwise present because of imperfect impedance matches due to the non-uniform dielectric constant values of the tissue itself.

If the standing waves are not disturbed, uneven heating of tumor 124 results since, as mentioned above, standing waves having maximum and minimum points cause certain portions of tumor 124 to be exposed to a maximum intensity and other portions to minimum intensity. By mode-stirring, the standing waves in the applicator and extending into tumor 124 are cyclically disturbed thereby changing the maximum and minimum points of the standing waves within tumor 124. This disturbance causes a periodic time-varying electric field pattern throughout tumor 124 whereby the uniformity of the temperature of the tumor is improved.

It is thus to be now appreciated, that the hyperthermia applicator of this invention provides for uniform heating of tissues. If it is desired, a greater concentration of the heating energy may be directed to the peripheral portion of the tissue to compensate for heat losses which otherwise would render the desired heating of the tissue to be non-uniform. The apparatus that has been described for hyperthermia treatment may also be used for other purposes such as therapeutic treatment of body organs such as the heart, liver, kidney, pituitary glands, etc.

What is claimed is:

1. Apparatus for hyperthermia treatment of tissue by microwave energy comprising:
   a. source means for providing microwave signals at only a selected frequency and intensity;
   b. means responsive to said source signals for generating simultaneously a plurality of radiating microwave signals in a spatially distributed pattern; said signal generating means including a plurality of dipole elements nonuniformly distributed over a given planar surface area with a greater number of elements at the edges of said surface area than at the central portion whereby the spatially distributed pattern of signals is nonuniform; and c. means for coupling said radiating signals to said tissue to irradiate said tissue, said coupling means including an applicator having a flexible portion containing dielectric material, said applicator being adapted to conform to the surface of said tissue, whereby greater heat is generated in said tissue at the regions corresponding to the edges of said surface area than at the inner portions.

2. Apparatus according to claim 1 wherein said signal generating means further comprises a rotating member so positioned in said coupling means in relation to said radiating microwave signals to disturb modes of said electric field so that said signals are distributed in said coupling means and said tissue in a periodic time-varying pattern whereby the uniformity of the temperature of the tissue is improved.

3. Apparatus for hyperthermia treatment of tissue by microwave energy comprising:

a. source means providing microwave signals at only a selected frequency and intensity;

b. signal generating means including a plurality of dipole elements distributed in a uniform array;

c. means for distributing current to said dipole elements such that dipole elements positioned at the periphery of the array emit more irradiating energy than dipole elements at the central portion whereby said antenna array emits relatively greater power irradiation at the edges of the array and relatively lesser power in the center of the array; and d. means for coupling said radiating signals to said tissue to irradiate said tissue, said coupling means including an applicator having a flexible portion containing dielectric material, said applicator being adapted to conform to the surface of said tissue whereby the spatially distributed patterns of signals is nonuniform with greater heat energy generated in the tissue corresponding to the edges of the array than at the inner portions.

* * * * *